United States Patent
Schmieding et al.

(10) Patent No.: US 7,326,247 B2
(45) Date of Patent: Feb. 5, 2008

(54) METHOD FOR CREATING A DOUBLE BUNDLE LIGAMENT ORIENTATION IN A SINGLE BONE TUNNEL DURING KNEE LIGAMENT RECONSTRUCTION

(75) Inventors: Reinhold Schmieding, Naples, FL (US); Craig D. Morgan, Greenville, DE (US); David N. Caborn, Louisville, KY (US)

(73) Assignee: Arthrex, Inc., Naples, FL (US)

( * ) Notice: Subject to any disclaimer, the term of this patent is extended or adjusted under 35 U.S.C. 154(b) by 373 days.

(21) Appl. No.: 10/975,087

(22) Filed: Oct. 28, 2004

(65) Prior Publication Data
US 2005/0096743 A1     May 5, 2005

Related U.S. Application Data

(60) Provisional application No. 60/515,429, filed on Oct. 30, 2003.

(51) Int. Cl.
*A61F 2/0811* (2006.01)
(52) U.S. Cl. ..................... 623/13.14; 606/73
(58) Field of Classification Search ... 623/13.11–13.19
See application file for complete search history.

(56) References Cited

U.S. PATENT DOCUMENTS

| | | | |
|---|---|---|---|
| 5,320,626 A | 6/1994 | Schmieding | |
| 5,350,383 A | 9/1994 | Schmieding et al. | |
| 6,461,373 B2 * | 10/2002 | Wyman et al. | 606/232 |
| 6,623,524 B2 * | 9/2003 | Schmieding | 623/13.14 |
| 6,716,234 B2 * | 4/2004 | Grafton et al. | 606/228 |
| 6,890,354 B2 * | 5/2005 | Steiner et al. | 623/13.14 |
| 2002/0165611 A1 * | 11/2002 | Enzerink et al. | 623/13.11 |
| 2003/0153948 A1 | 8/2003 | Morrison et al. | |
| 2004/0237362 A1 * | 12/2004 | O'Connell | 40/310 |

* cited by examiner

*Primary Examiner*—Suzette Gherbi
(74) *Attorney, Agent, or Firm*—Dickstein Shapiro LLP

(57) ABSTRACT

A method and construct for joint repair in which attachment of a double bundle graft ligament approximates anatomic orientation using interference fixation in a single bone tunnel. The double bundle graft features separable strands. A threaded screw is inserted between the separable strands and provides interference fixation of the graft against radially opposing walls defining the bone tunnel. Attachment of the graft using separated strands more closely approximate the configuration of the native ligament. The resulting reconstruction exhibits mechanical functionality that more accurately mimics that of the intact joint, with a minimum of associated tissue morbidity.

18 Claims, 6 Drawing Sheets

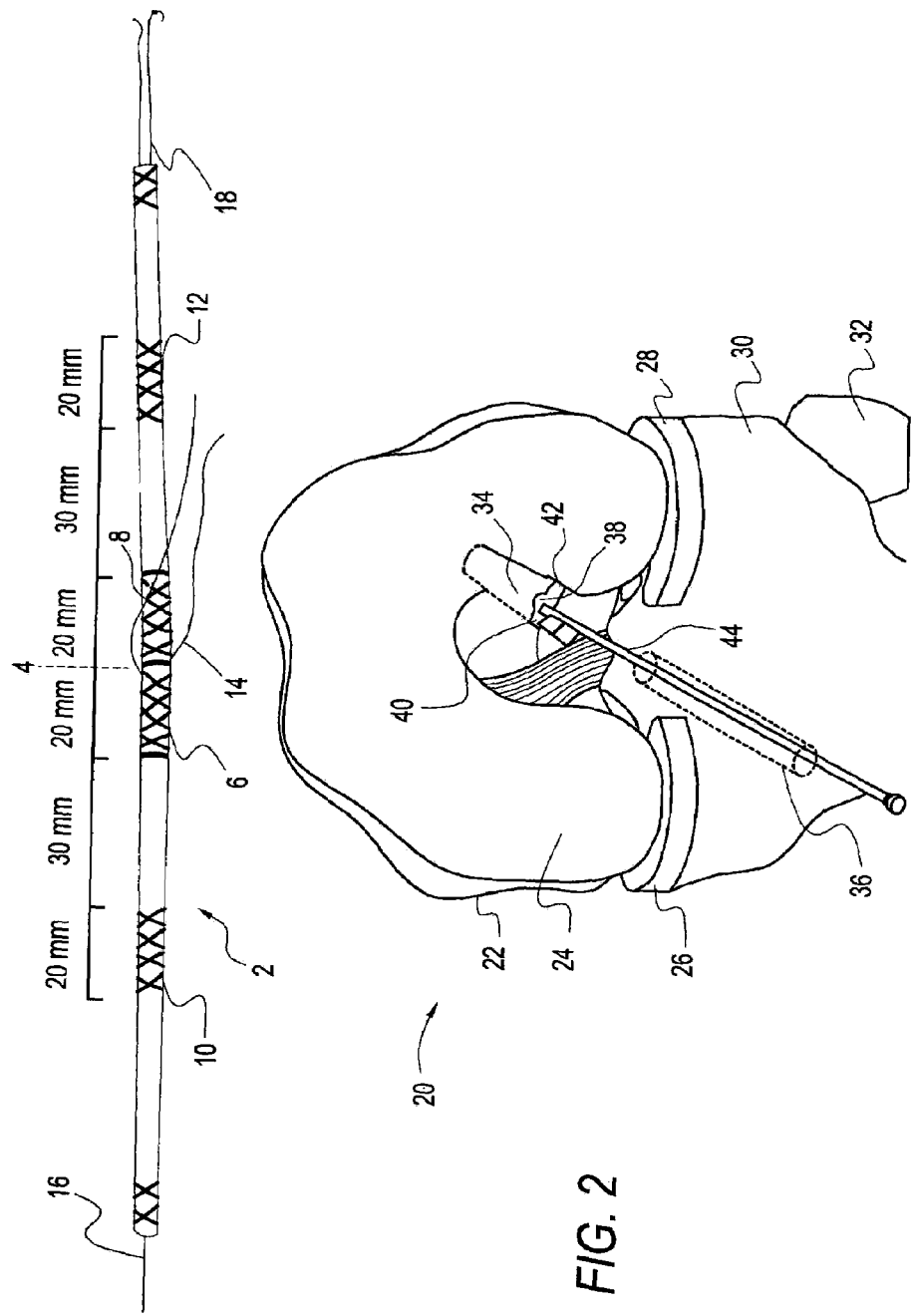

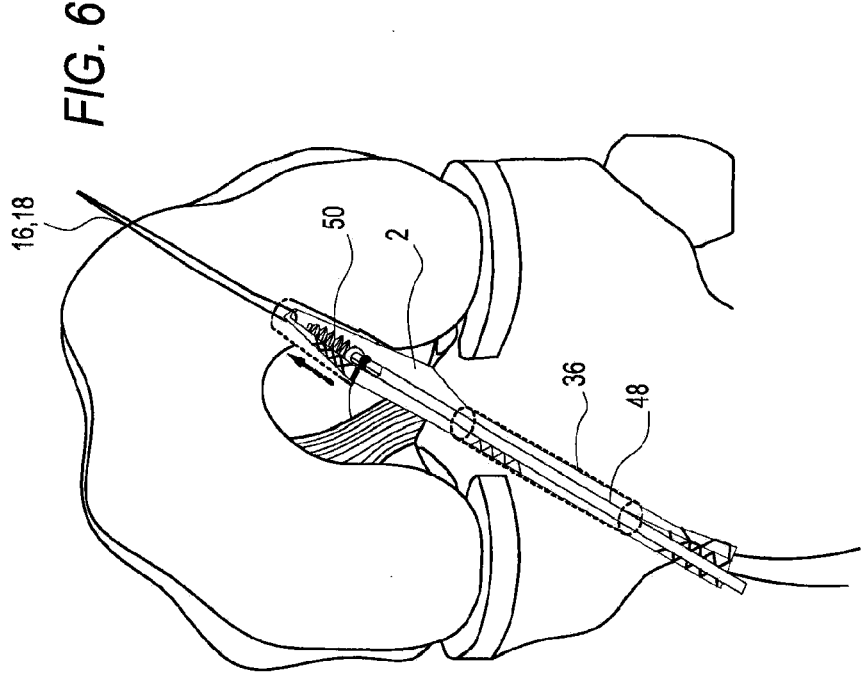
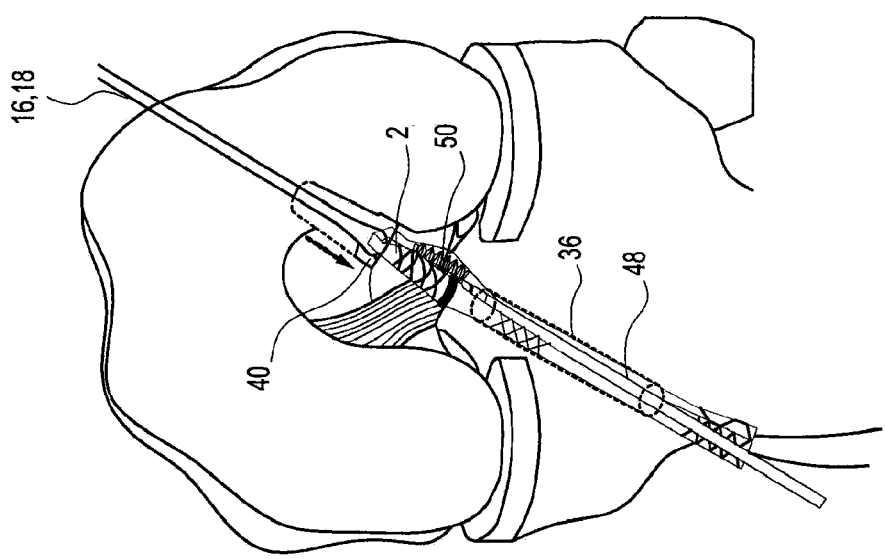

METHOD FOR CREATING A DOUBLE BUNDLE LIGAMENT ORIENTATION IN A SINGLE BONE TUNNEL DURING KNEE LIGAMENT RECONSTRUCTION

This a application claims the benefit of U.S. Provisional Application Ser. No. 60/515,429, filed Oct. 30, 2003.

BACKGROUND OF THE INVENTION

1. Field of the Invention

The present invention relates to cruciate ligament reconstruction, and more specifically to anatomically accurate cruciate ligament reconstruction using double-bundle ligament grafts in single bone tunnels.

2. Description of the Related Art

Cruciate ligament reconstruction is routinely performed by creating femoral and tibial tunnels, and various graft types are used to replace the native cruciate ligament. Most reconstructions are performed using a single-bundle ligament graft made of autograft or allograft material.

Biomechanical studies have shown that an anatomic double-bundle cruciate ligament reconstruction can be superior in restoring normal knee laxity compared with conventional single-bundle isometric reconstructions. Double-bundle reconstructions, as compared to single-bundle reconstructions, more closely approximate the structure and configuration of the native tendon, and better accommodate the knee's "screw-home" mechanism.

Double-bundle reconstructions currently involve individual fixation for each strand of the graft. The need to individually fixate each strand of the double-bundle graft adds to the complexity and cost of the procedure. Double-bundle reconstructions also are performed as shown in U.S. Pat. No. 6,623,524 to Schmieding, the disclosure of which is incorporated herein by reference. Methods for repairing torn cruciate ligaments using double-bundle grafts that are simpler to complete and more closely approximate the native ligament development would enhance reconstruction results.

SUMMARY OF THE INVENTION

The present invention provides methods and apparatus for fixing a double bundle ligament in single bone tunnels during knee ligament reconstruction. The techniques produce a more anatomically correct ligament reconstruction, particularly as in the case of the anteromedial and posterolateral bundles of the anterior cruciate ligament (ACL).

In order to reestablish native anatomical biomechanics of the damaged ligament, the fixation method of the present invention provides a double bundle configuration of the ligament using a single tunnel at each of the femoral and tibial attachment sites.

A double, triple, or quadruple graft is prepared, and a femoral socket and a tibial tunnel, in the form of axially elongate openings, are created for ligament reconstruction in the standard fashion. Reference is made to examples of standard ligament reconstruction techniques disclosed in U.S. Pat. No. 5,320,626 to Schmieding and U.S. Pat. No. 5,350,383 to Schmieding et al., the disclosures of which are incorporated herein by reference.

A notcher, burr or rasp is used to remove material from the tunnel walls to notch or widen the tunnel openings. The notches accommodate graft strands that are forced against the tunnel walls and into the notches by a fixation implant inserted between strands of the replacement graft, as described further below.

The notches are oriented such that strands of a ligament graft fixed in the tunnel achieve an orientation that more closely approximates that of the native ligament bundles. A fixation implant installed between strands of the graft spread the strands to approximate the anatomical attachment and functionality of the ligament being replaced. In a preferred embodiment, fixation is achieved using an interference implant, preferably in the form of a threaded screw. The technique provides simultaneous anatomical spreading and fixation in each tunnel.

An exemplary application of the technique to reconstruction of the anterior cruciate ligament in the human knee features positioning a threaded interference screw between the anteromedial and posterolateral bundles of the ACL in each of the pre-formed tibial tunnel and femoral socket. Installation of the tibial and femoral screws preferably is made in a retrograde fashion, reference being made to examples of retrograde interference fixation described in U.S. Pat. No. 6,461,373 to Wyman et al., the disclosure of which is incorporated herein by reference.

The reconstruction techniques according to the present invention provide a more anatomical reconstruction that maximizes graft stiffness with true joint line fixation, which reduces tunnel widening. In addition, with respect to knee reconstructions, the techniques substantially increase femoral and tibial graft fixation strength compared to standard interference screws. Further, the invention maintains graft tension during tibial screw fixation, and replaces the need for double tunnel surgery using reproducible transtibial techniques and instrumentation.

BRIEF DESCRIPTION OF THE DRAWINGS

A more complete understanding of the invention will be gained by reference to the descriptions below when read in conjunction with the attached drawings listed as follows:

FIG. 1 illustrates a graft ligament used in an exemplary method of anterior cruciate ligament reconstruction according to the present invention;

FIG. 2 is a schematic anterior view of a human left knee shown during a step of notch formation in femoral and tibial tunnels in the method of anterior cruciate ligament reconstruction according an exemplary embodiment of the present invention;

FIG. 5 illustrates positioning of the femoral retroscrew with respect to the graft strands in the method of ligament reconstruction according to the present invention;

FIG. 6 illustrates insertion of the femoral retroscrew according to the present invention;

DETAILED DESCRIPTION OF THE INVENTION

Figure 4:
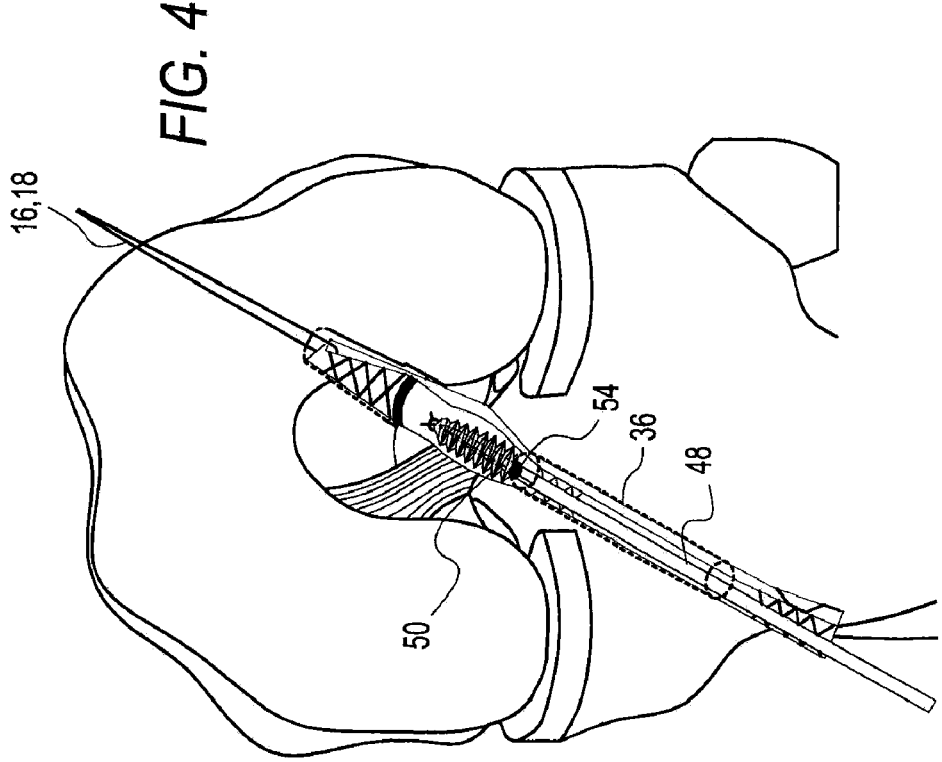
FIG. 4 illustrates alignment of a femoral retroscrew in the knee in a further step of the reconstruction method according to the present invention.

An exemplary method of anterior cruciate ligament (ACL) reconstruction in a human knee according to the present invention is described below in conjunction with FIGS. 1-12. The teachings, methods, and techniques presented can be applied as well to other surgical applications, including without limitation posterior cruciate ligament (PCL) reconstruction in the human knee, for example, as well as reconstructions of other ligaments and joints in humans and skeletal creatures. Adaptations and adjustments to the exemplary technique of human ACL reconstruction described undoubtedly will be necessary in the other surgical applications. They will be well within the skill of the practitioner capable of understanding and undertaking the present teachings and techniques, however, and readily accomplished without undue experimentation.

Referring initially to FIG. 1, a double hamstring autograft or tibialis tendon allograft 2 of a minimum length of 140 mm is preferred for the double bundle ACL technique. A midline 4 is marked and 20 mm whip-stitches 6, 8 of #2 FiberWire™ suture is placed on each side of the graft mid line 4. (FiberWire™ suture is sold by Arthrex, Inc. of Naples, Fla., the assignee of the present application, and is described and claimed in U.S. Pat. No. 6,716,234, the disclosure of which is incorporated herein by reference). Suturing across the midline 4 is avoided to allow for folding of the graft during tunnel insertion, described in more detail below. Another pair of 20 mm whip-stitches 10, 12 is placed 50 mm from the proximal ends of the graft 2 to enhance tibial RetroScrew fixation, described further below. A #5 FiberWire™ graft passing suture 14 is looped around the midline 4. Sutures 16, 18 are secured with whip-stitching to the ends of graft 2.

Referring to FIG. 2, a skeletal knee joint 20 is illustrated showing terminal portions of a femur 22 with femoral condyles 24 engaging medial and lateral menisci 26, 28 of a tibia 30. A portion of a fibula 32 also is shown. Femoral socket 34 and tibial tunnel 36 are prepared in standard transtibial fashion. Femoral socket orifice 38 is notched at the 10:00 (40) and 4:00 (42) positions for left knee 20, to accommodate anteromedial and posterolateral bundles of graft 2, described below in further detail. The anterior and posterior tibial tunnel orifices are notched using a 5 mm wide Retro Tunnel notcher 44, sold by Arthrex, Inc. of Naples, Fla.

Figure 3:
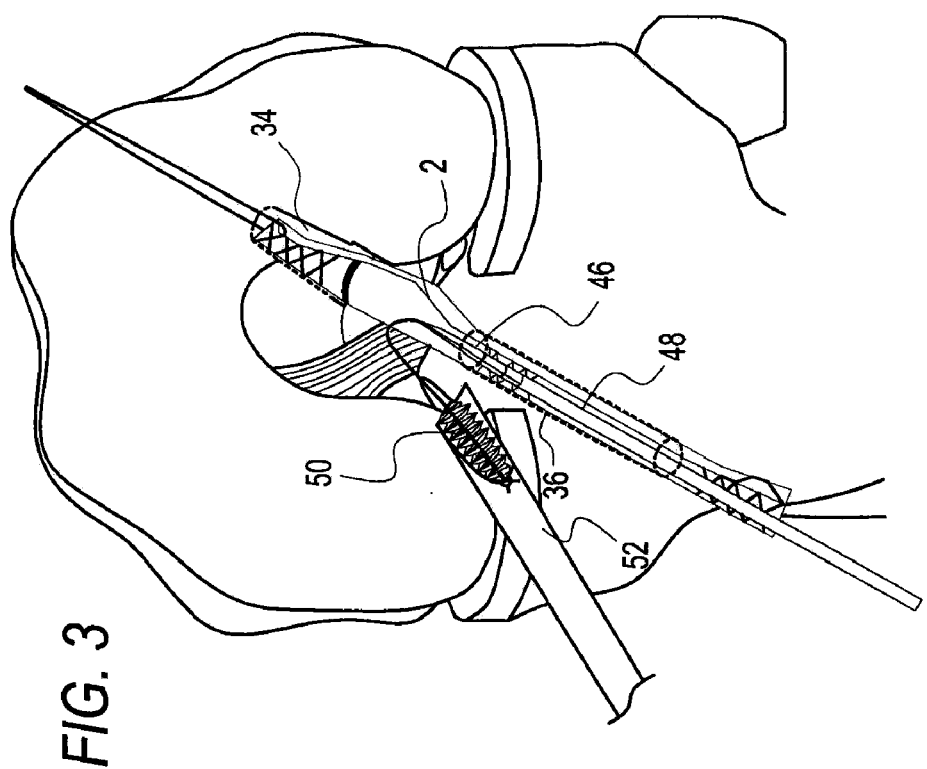
FIG. 3 illustrates the left knee with a ligament graft passed into the tunnels in preparation for femoral fixation in retrograde fashion according to the present invention.

Referring to FIG. 3, graft 2, folded at the midline 4. is passed into the femoral socket 40. A #2 FiberStick™ 46 (FiberStick™ is a length of FiberWire™ with a stiffened tip, disclosed in U.S. Patent Application Publication No. US 2003/0153948, incorporated herein by reference) is preloaded in a RetroScrew driver 48 with a 2 cm length extending from the tip of driver 48. The driver 48 is inserted through the tibial tunnel 36 anterior the graft 2. The extended end of FiberWire™ 46 is retrieved and pulled out an anteromedial portal. The FiberStick™ 46 is inserted to a head of a femoral retroscrew 50. The FiberStick™ 46 is knotted at the tip of the Femoral RetroScrew 50 with at least three half hitches. The Femoral RetroScrew 50 is then snapped into the end of a Shoehorn Cannula 52, sold by Arthrex, Inc. of Naples, Fla. The cannula 52 is inserted into the anteromedial portal and a cannula obturator (not shown) is used to push the screw 50 into the joint.

Referring to FIG. 4, the retroscrew 50 is urged by drawing on FiberStick 46 until the RetroScrew 50 is in axial alignment with tibial tunnel 36. The Femoral RetroScrew 50 is then mounted on the tip of driver 48, care being taken to remove soft tissue from the driver/screw interface prior to seating the screw 50. The RetroScrew 50 is fully inserted onto the driver when a laser line 54 is flush with the head of the screw. The FiberStick™ suture 46 is removed out the anteromedial portal.

Referring next to FIG. 5, graft 2 is pulled distally to visualize the whip-stitching 6, 8 and to position the Femoral RetroScrew 50 between the two strands of the folded graft 2. The graft 2 is pulled slowly so that it is seated fully in the femoral socket 40 while advancing the screw 50 into the femoral socket 40 between the graft strands. A probe (not shown) may be used to orient the two bundles of graft 2 anatomically into the respective notches of femoral tunnel 40. The distal end of the whip-stitching 6, 8 should be flush with the opening of tunnel 40 prior to insertion of screw 50.

The graft 2 is tensioned in the femoral socket 40, and graft strands are positioned into the notches of the femoral tunnel 40. The Femoral RetroScrew 50, is positioned between the graft strands and axially aligned with the tunnel 40 in 90° of knee flexion. The diameter of femoral RetroScrew 50 should be equal to or 1 mm larger than the diameter of the drilled femoral socket. The femoral RetroScrew 50 separates the folded graft 2 into two anatomical bundles. The concentrically-positioned screw 50, under the looped graft 2, substantially increases femoral pull-out strength of the graft 2 as compared to prior techniques.

Figure 7:
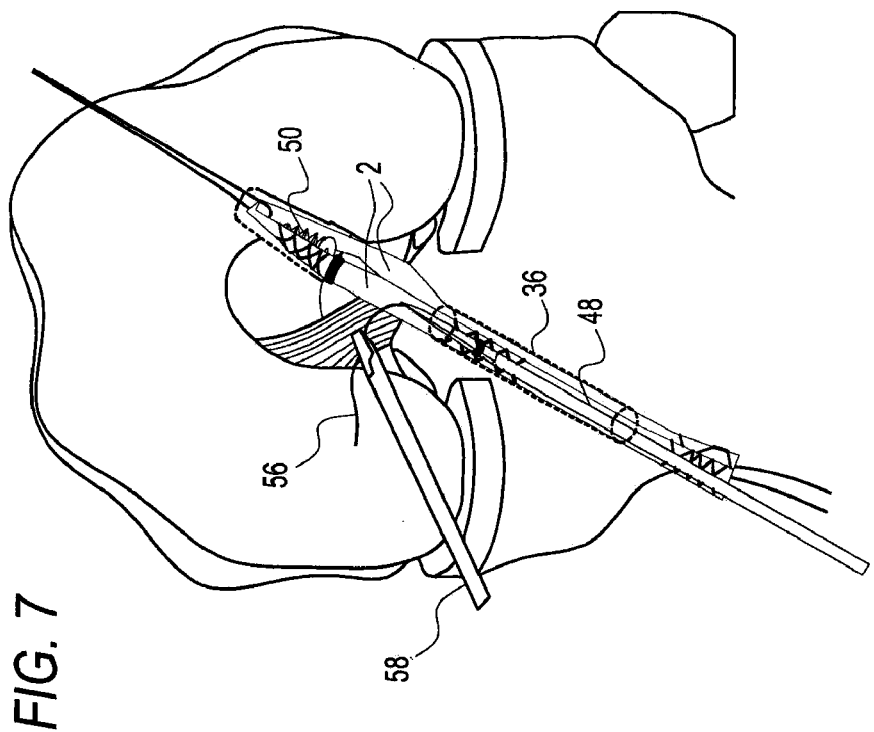
FIG. 7 illustrates the knee in preparation for insertion of a tibial retroscrew according to the present invention.
Figure 10:
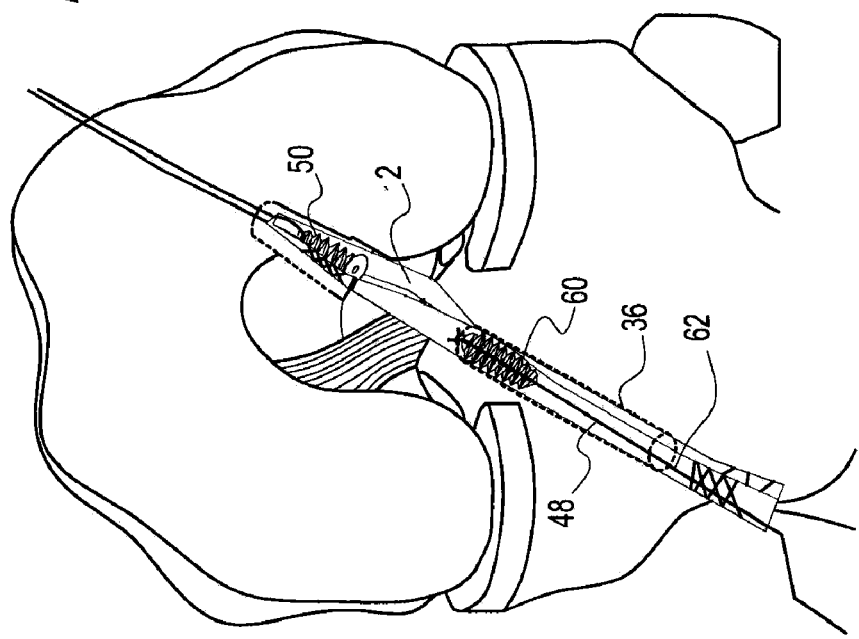
FIG. 10 illustrates insertion of the tibial retroscrew in the tibial tunnel according to the present invention.

Referring to FIG. 7, the knee is cycled and the driver 48 is reloaded with a #2 FiberStick™ 56 and reinserted up the tibial tunnel 36 anterior to the graft 2. The proximal end of the FiberStick™ 56 is retrieved and pulled out the anteromedial portal using a grasper 58.

Figure 8:
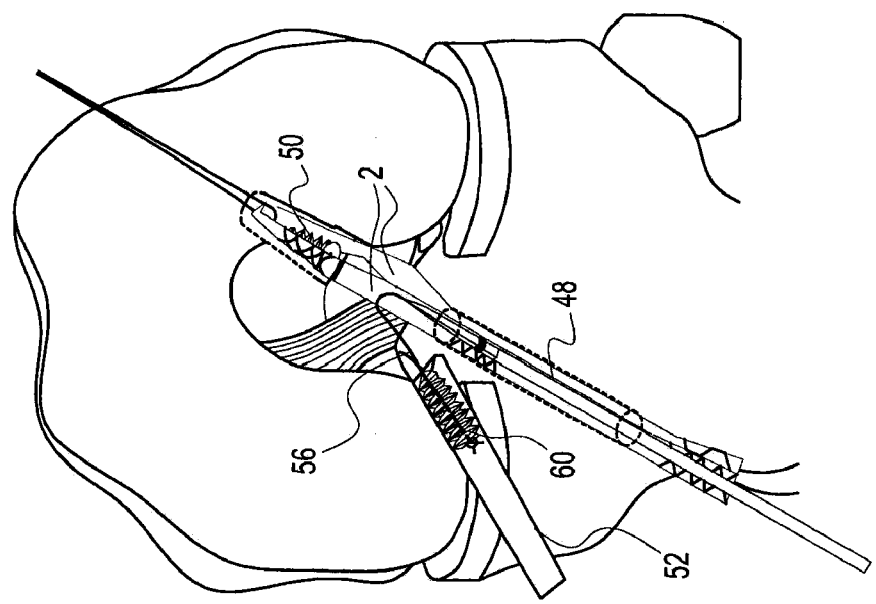
FIG. 8 illustrates a step of delivering the tibial retroscrew into the knee joint according to the present invention.

Referring to FIG. 8, the end of FiberStick™ 56 is passed through the tip of a Tibial RetroScrew 60 having a diameter appropriate to the tibial tunnel diameter. A Mulberry knot is tied behind the round head of the retroscrew 60. The Tibial RetroScrew 60 is snapped into the end of the Shoehorn Cannula 52 and the cannula 52 inserted into the anteromedial portal. A cannula obturator is used to push the retroscrew 60 into the joint.

Figure 9:
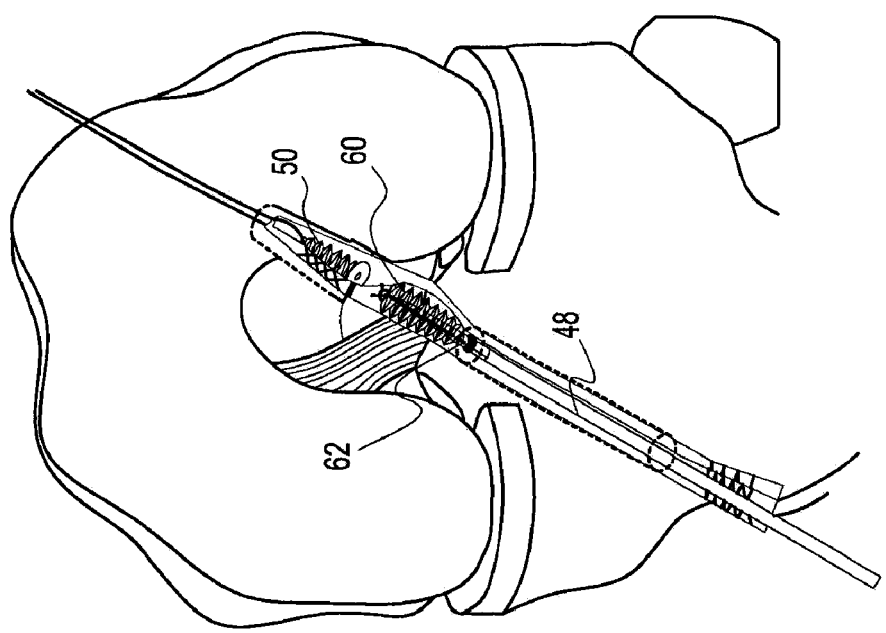
FIG. 9 illustrates alignment of the tibial retroscrew with the tibial tunnel according to the present invention.
Figure 12:
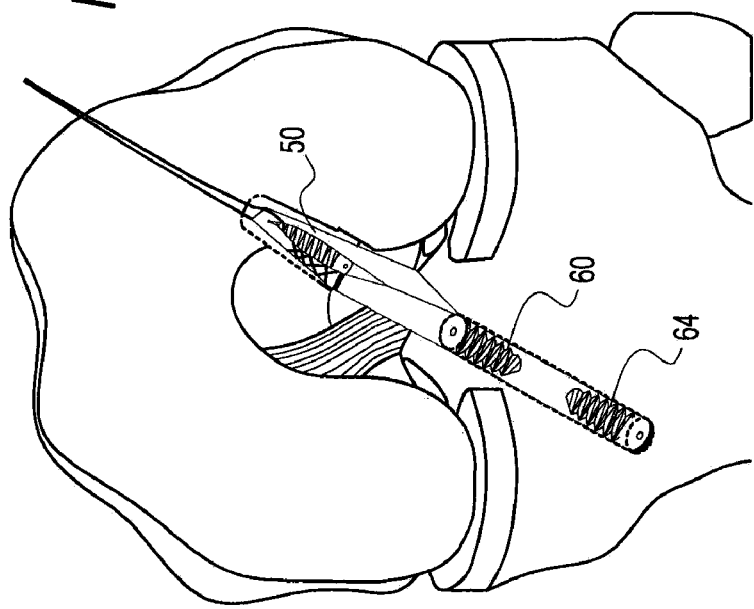
FIG. 12 illustrates secondary screw fixation in the exemplary ligament reconstruction method according to the present invention.

Referring to FIG. 9, the knee is cycled and the driver 48 is reloaded with a #2 FiberStick™ 62 and reinserted up the tibial tunnel 36 anterior to the graft 2. The Tibial RetroScrew 60 is mounted onto the tip of driver 48 by pulling on the FiberStick™ suture 62. Soft tissue is removed from the screw/driver interface prior to seating of the screw 60. The screw 60 is fully inserted on the driver 48 when a laser line on the driver 48 is flush with the tip of the screw. The FiberStick™ 62 is wrapped around handle posts on the driver 48 (FIG. 10) to secure the screw 60 for retrograde insertion.

Figure 11:
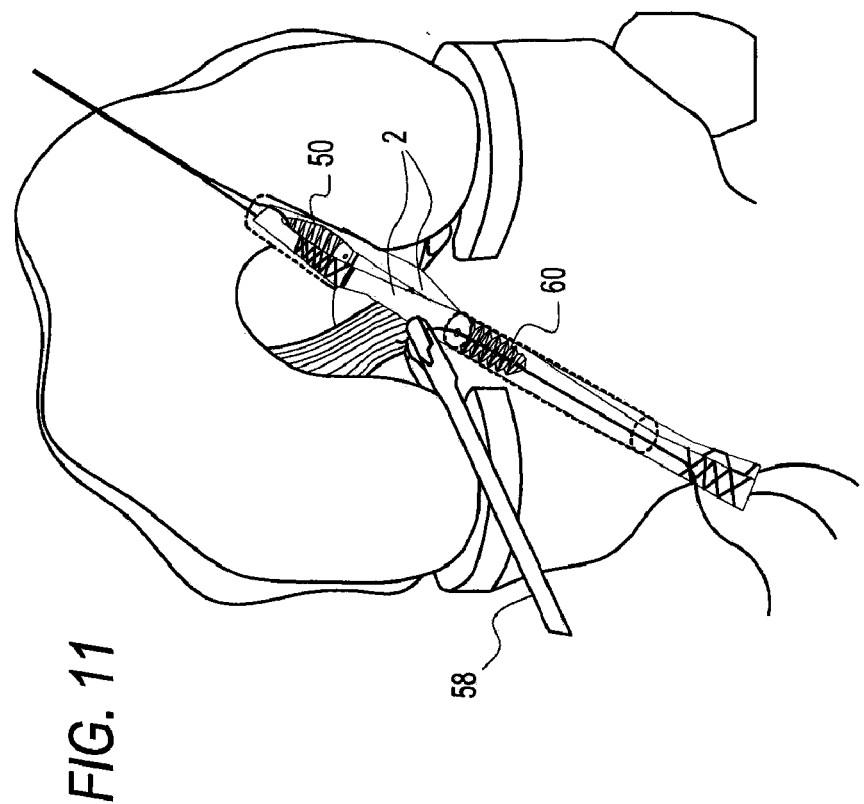
FIG. 11 illustrates a further step of the exemplary ligament reconstruction method according to the present invention.

While fully tensioning the graft 2 in approximately 20° of knee flexion, the Tibial RetroScrew 60 is inserted counterclockwise, anterior to the graft 2 under full visual control. Insertion is completed when the round head of the screw 2 is slightly countersunk with respect to the tibial tunnel orifice. The FiberWire™ 62 is released from the driver handle and withdrawn out the anteromedial portal by pulling from the knotted end using a grasper 58, as shown in FIG. 11.

Secondary screw fixation of the graft in the tibial tunnel may be performed by inserting a second Femoral Retro-Screw 64 into the distal end of the tibial tunnel 36 (in an antegrade fashion). Such bi-cortical fixation of the graft 2 in the tibial tunnel 36 provides maximum graft fixation strength, creates a blood-rich healing environment in the tunnel 36 between the two screws 60, 64, and reduces post-op soft tissue hematoma.

Although the present invention has been described in connection with preferred embodiments, many modifications and variations will become apparent to those skilled in the art.

What is claimed is:

1. A method of surgical ligament repair comprising:
   forming a tibial tunnel and a femoral tunnel, each tunnel having tunnel walls;
   widening the tibial and femoral tunnels by removing bone material from the tunnel walls to form tibial and femoral tunnels that are wider in one radial direction than another; and
   securing a double bundle ligament graft in the widened tibial and femoral tunnels.

2. A method as in claim 1, wherein the step of securing the double bundle ligament graft includes securing the graft in the tunnels by interference fixation.

3. A method as in claim 2, wherein the double bundle ligament graft includes at least two strands, and the double bundle ligament graft is secured by installing a respective implant between two strands of the graft such that the graft strands are secured separately between an outer wall of the respective implant and the tunnel walls.

4. A method as in claim 3, wherein the direction in which the tunnels are widened and the orientation in which the graft strands are secured within the tunnels approximates the anatomical orientation of a native ligament being replaced.

5. A method of graft fixation comprising:
   removing bone to forming an axially-elongated opening;
   inserting a ligament graft into the opening, the ligament graft having at least two separable strands; and
   installing a fixation device between the strands of the graft.

6. A method according to claim 5, wherein the step of removing bone comprises removing bone material so as to develop an oval cross-section in the opening.

7. A method according to claim 5, wherein the opening is a tunnel.

8. A method according to claim 7, wherein the fixation device is installed in a retrograde fashion by drawing the fixation device into the tunnel.

9. A method according to claim 8, comprising drawing the fixation device from an internal end opening of the tunnel toward an external end opening of the tunnel.

10. A method according to claim 5, wherein the opening is a socket.

11. A method according to claim 5, wherein the fixation device comprises a threaded screw, and the step of installing the fixation device comprises rotated driving of the threaded screw to achieve interference fixation.

12. A construct comprising:
    a first elongate opening formed in a first bone;
    a first fixation device; and
    a graft having at least two separable strands, the first fixation device installed between the at least two separable strands to secure to the graft to bone walls defining the first elongate opening.

13. A construct according to claim 12, wherein the first elongate opening has a cross-section that is wider in one direction than in another.

14. A construct according to claim 13, wherein the first elongate opening has a cross-section that oval in shape.

15. A construct according to claim 13, wherein the first fixation device comprises a threaded screw.

16. A construct according to claim 12, further comprising a second elongate opening formed in a second bone and a second fixation device installed between the at least two separable strands to secure to the graft to bone walls defining the second elongate opening.

17. A construct according to claim 16, wherein the first bone is a femur and the second bone is a tibia.

18. A construct according to claim 16, wherein the second fixation device comprises a threaded screw.

* * * * *